United States Patent [19]

Knaak

[11] 3,992,325

[45] Nov. 16, 1976

[54] γ-CrOOH FLUORINATION CATALYSTS

[75] Inventor: Joachim Friedrich Knaak, Wilmington, Del.

[73] Assignee: E. I. Du Pont de Nemours and Company, Wilmington, Del.

[22] Filed: Sept. 25, 1975

[21] Appl. No.: 616,835

[52] U.S. Cl. .............................. 252/442; 252/441; 260/653.7
[51] Int. Cl.$^2$ .................... B01J 27/06; C07C 17/00; C07C 19/08
[58] Field of Search ........................... 252/441, 442

[56] References Cited
UNITED STATES PATENTS

| | | | |
|---|---|---|---|
| 3,183,276 | 5/1965 | Vecchio | 260/653.4 |
| 3,258,500 | 6/1966 | Swamer | 260/653.7 |
| 3,294,852 | 12/1966 | Vecchio et al. | 260/653.7 |
| 3,431,067 | 3/1969 | Kato et al. | 252/441 X |
| 3,442,962 | 5/1969 | Vecchio et al. | 260/653.7 |
| 3,673,113 | 6/1972 | Naito et al. | 252/441 |
| 3,752,850 | 8/1973 | Scherer et al. | 252/441 |

Primary Examiner—Winston A. Douglas
Assistant Examiner—Mark Bell

[57] ABSTRACT

An improved catalyst comprising an intimate mixture of γ-CrOOH and metal fluoride and its use in the reaction of halogenated aliphatic compounds with HF over a chromium (III) oxide catalyst to produce fluorine-containing aliphatic compounds.

8 Claims, No Drawings

γ-CrOOH FLUORINATION CATALYSTS

BACKGROUND OF THE INVENTION

The vapor phase reaction of HF with halogenated aliphatic compounds over solid catalysts is well known in the art. The use as a catalyst for these reactions of chromium (III) oxide, sometimes referred to as dichromium trioxide of $Cr_2O_3$, is also known.

These chromium (III) oxides can be made by the reduction of chromium (VI) oxide ($CrO_3$) with ethanol. Because of the physical form of the product obtained, this product is often referred to as "gel catalyst." The catalysts can also be made from the commercial pigment Guignet's Green, a chromium (III) oxide with the empirical formula $Cr_2O_3 \cdot 2H_2O$; and by precipitation of a water-containing chromium (III) trihydroxide by treating aqueous solutions of chromium (III) nitrate or other water-soluble salts with an alkaline reagent. Because the trihydroxide $Cr(OH)_3$ is empirically chromium (III) oxide trihydrate $Cr_2O_3 \cdot 3H_2O$, this catalyst is often referred to as "COT" catalyst. Although chromium (III) oxides so obtained have long been considered to be amorphous, recent studies have shown that the chromium (III) oxides so prepared exhibit an orthorhombic crystal structure, and are characterized as gamma-chromium oxide hydroxide, usually written as γ-CrOOH.

γ-CrOOH has been recognized as an excellent fluorination catalyst due to its high activity in the replacement of other halogens with fluorine. It is among the few catalysts, for example, that will replace all four chlorine atoms in $CCl_4$ to form $CF_4$. In addition to good activity for the desired reaction, however, a catalyst should be productive in the sense of promoting the reaction of a large quantity of reactant with a small quantity of catalyst. An especially significant commercial catalyst characteristic is longevity, or the retention of catalyst activity and productivity over an extended period of time. Replacement of catalyst not only represents a significant expense in itself, but the time spent in replacing the catalyst detracts from the productivity of a plant in which the catalyst is used.

SUMMARY OF THE INVENTION

The present invention provides an improved γ-CrOOH catalyst having substantially longer life.

Specifically, the instant invention provides a catalyst comprising an intimate mixture of γ-CrOOH and about from 5% to 50% by weight of at least one non-alkali metal fluoride selected from thorium tetrafluoride ($ThF_4$), aluminum trifluoride ($AlF_3$), calcium fluoride ($CaF_2$), magnesium fluoride ($MgF_2$), titanium tetrafluoride ($TiF_4$), cerium tetrafluoride ($CeF_4$), yttrium trifluoride ($YF_3$), strontium fluoride ($SrF_2$), barium fluoride ($BaF_2$), ferric fluoride ($FeF_3$) and zinc fluoride ($ZnF_2$).

The invention further provides a process for the use of these catalysts in the vapor phase reaction of a halogenated aliphatic compound containing halogen atoms other than fluorine with HF at a temperature of about from 150° to 500° C. to produce halogenated aliphatic compounds containing increased numbers of fluorine atoms.

DETAILED DESCRIPTION OF THE INVENTION

The metal fluorides used in preparing the catalysts of the invention should be finely divided, generally having a particle size of less than about 44 microns. A particularly convenient size has been found to be those which pass a 325 mesh (U.S. standard) screen. A 325 mesh screen has 125 mesh/cm. (323/inch) with sieve openings of 0.044 mm. (0.0017 inch) and wire diameters of 0.036 mm. (0.0014 inch). Metal fluoride particles which are substantially larger than the 44 microns required to pass a 325 mesh screen have a reduced beneficial effect on catalyst life.

The catalytic compositions of the present invention are intimate mixtures of γ-CrOOH and a metal fluoride. While the nature of the compositions is that of a physical admixture, it has been found that the present compositions generally cannot be satisfactorily prepared by the admixture of preformed γ-CrOOH and preformed metal fluoride. The most satisfactory method of preparation involves the precipitation of γ-CrOOH in the presence of metal fluoride particles.

The catalytic compositions can be based on either the gel or COT forms of γ-CrOOH. In the preparation of gel catalyst, chromium (VI) oxide of the formula $CrO_3$ is brought into contact with a reducing agent under reaction conditions. In the preparation of the instant compositions, the desired amount of metal fluoride can be preslurried in water, to which the quantity of chromium trioxide ($CrO_3$) is added and dissolved, in an amount sufficient to satisfy the requirements of the catalytic composition to be prepared. A wide variety of reducing agents for the chromium trioxide can be used, as is well recognized in the art. A particularly satisfactory reducing agent is ethanol. This reducing agent is added to the mixture in a regulated manner to avoid overheating of the reaction mixture and to insure complete reduction of the chromium trioxide. The resulting precipitated solids are then collected, dried and prepared for catalyst use in the usual manner.

In preparing the present catalytic compositions using the COT form of γ-CrOOH, the γ-CrOOH and the metal fluoride are similarly intimately admixed during the course of preparation of the γ-CrOOH. With this catalyst, the desired amount of metal fluoride is slurried in the aqueous solution that results from the initial solution of trivalent chromium (III) salt in water. Typical salts used include chromium (III) nitrate or $CrCl_3 \cdot 6H_2O$. After combination of these components, the mixture is heated and an alkaline reagent is added until precipitation is complete. Ammonia is most frequently used as the alkaline reagent, since alkali metal ions tend to poison the catalyst. The precipitated solids are then collected, dried and prepared for catalyst use in the usual manner.

The precipitated γ-CrOOH catalyst, with both the gel or COT forms, generally exhibits a particle size of less than about 5 microns.

The catalyst can be used in any form which is convenient to the reaction system in use. Generally, for larger scale operations, the catalyst will be used in the form of pellets or similar shapes which are made according to conventional techniques.

The γ-CrOOH catalysts containing $CaF_2$, $MgF_2$, $ThF_4$, $AlF_3$, $CeF_4$ or $YF_3$ have increased useful life of from 3 to 30 times without decreased activity or productivity. The catalysts containing $TiF_4$, $SrF_2$, $BaF_2$, $FeF_3$ or $ZnF_2$ exhibit some decrease in activity as well, which permits the preparation of products such as $CF_3Cl$, $C_2F_5Cl$ or $CHClF_2$ without loss of productivity or unacceptably high production of $CF_4$, $C_2F_6$ or $CHF_3$. Therefore, the choice of specific catalyst and conditions for the reaction of HF with halogenated aliphatic compound will to some extend depend on the nature of the starting materials and the products desired. $CeF_4$ specifically will react with the carbon-hydrogen bond to replace H by F and will add the elements of fluorine to the carbon-carbon double bond. $\gamma$-CrOOH containing $CeF_4$ should not, therefore, be used with starting materials containing hydrogen-carbon bonds or carbon-carbon double bonds when retention of these features in the fluorinated product is desired.

Since thorium tetrafluoride ($ThF_4$) is mildly radioactive, appropriate precautions should be taken in its handling and use. Catalysts containing aluminum fluoride or thorium tetrafluoride have been found to impart particularly long life, and are therefore preferred.

The increase in catalyst life realized through the use of the present $\gamma$-CrOOH catalysts is a function of the amount of metal fluoride in the catalytic compositions. With the gel form of $\gamma$-CrOOH, for example, as little as about 5% by weight $CaF_2$ increases useful life from 30 to 60 hours. At 25% $CaF_2$, the maximum life of 340–350 hours is reached. The optimum amount of metal fluoride varies somewhat with the particular metal fluoride used.

The present catalysts are particularly useful in the fluorination of halogenated aliphatic compounds, including any aliphatic compound containing at least one halogen atom other than fluorine in the molecule which can be replaced by fluorine by reaction with HF. These include both halogenated aliphatic hydrocarbons and halogenated aliphatic compounds containing functional groups. The compounds can contain from one to eight carbons in which adjacent carbon atoms are linked by 1 or 2 valence bonds and include halogenated alkanes, halogenated cycloalkanes, halogenated alkenes and halogenated cycloalkenes. The halogens can be flourine, bromine or chlorine with at least one chlorine or bromine. Typical compounds are shown in Swamer et al., U.S. Pat. NO. 3,258,500 hereby incorporated by reference.

Compounds that can be fluorinated according to the present process and which have functional groups include perhaloacetones of the formula $CX_3COCX_3$, perhaloacetyl halides of the formula $CX_3COX$, perhaloacetonitriles of the formula $CX_3CN$ and trihaloacetaldehydes of the formula $CX_3CHO$ wherein X is chlorine or fluorine, at least one X being chlorine.

The halogenated aliphatic hydrocarbons can be preformed or formed in situ. For in situ formation, mixtures of aliphatic hydrocarbons such as methane, ethane, ethylene or acetylene, and chlorine can be combined with the HF in the manner shown by Vecchio et al. in U.S. Pat. Nos. 3,294,852 and 3,442,962.

The $\gamma$-CrOOH catalysts are preferably activated by heating with an inert gas in the manner shown, for example, by Swamer et al., U.S. Pat. No. 3,258,500. This activation is particularly desirable for large scale operations. For small scale operations and particularly if an initial period of reduced activity is acceptable, activation can be allowed to occur during reactions of HF with halogenated aliphatic compounds if the reaction temperature is above about 300° C. For lower reaction temperatures of about from 150° to 300° C., prior activation of the catalyst should generally be used.

The catalysts of the present invention should not be exposed to temperatures substantially in excess of 500° C. for extended periods of time. Such highly elevated temperatures cause the transition of the chrome oxide to a different crystal form which is inactive. The temperature of the onset of this transition can be as low as 350°–400° C. or as high as 700° C. The use of the present catalysts in the presence of HF, however, causes this transition to occur at higher temperatures, generally not lower than 500° C.

The known reaction conditions for use with $\gamma$-CrOOH can also be used with the catalysts of the present invention. In general, reaction temperatures of about from 150° to 700° C. are satisfactory for the fluorination of halogenated aliphatic hydrocarbons. When reacting perhaloketones, acid halides, nitriles or aldehydes, somewhat lower maximum temperatures of about 550° C. are used because of the thermal instability of the products. In general, these reactions are carried out at ambient pressures. However, the reactions can also be carried out at either subatmospheric or super-atmospheric pressures.

In fluorination reactions using the present catalysts, the molar ratio of HF to halogenated aliphatic compound will generally be at least about one mole HF per mole of halogen to be replaced. Usually an excess of HF is used, particularly where it is desired to replace all halogens other than fluorine. When incomplete replacement of halogen is desired, it is preferably to keep the molar ratio of HF near that desired to replace the desired number of halogens. The optimum conditions required to convert any particular starting halogenated aliphatic compound to the desired product will be evident to those skilled in the use of prior $\gamma$-CrOOH catalysts, as illustrated, for example, in Swamer et al., U.S. Pat. No. 3,258,500.

The following Examples further illustrate the preparation and representative uses of the catalysts of this invention.

EXAMPLES 1–25

In Examples 1–13, catalysts based on $\gamma$-CrOOH were prepared in a reaction vessel equipped with an agitator, reflux condenser and addition means. Into this reaction vessel were placed 600 parts water and the quantity of 325 mesh metal fluoride indicated in Table I. The mixture was agitated until a slurry was obtained, then 48.2 parts chromium trioxide were added and the mixture was stirred until the oxide dissolved. With rapid agitation, 28.4 parts ethanol were added in small increments at 5 min. intervals. After agitating for three hours, an additional 28.4 parts ethanol were added in the same manner. The mixture was then heated under reflux with agitation for 16 hours. The mixture was cooled to ambient temperature, the solids collected by filtration and the filter cake was washed twice with deionized water. The cake was air dried and then under vacuum at 60°–72° C. for 24 hours.

TABLE I

| Example | Metal Fluoride | Parts | % Weight Metal Fluoride |
|---|---|---|---|
| 1 | $CaF_2$ | 41 | 50% |
| 2 | $MgF_2$ | 41 | 50% |
| 3 | $SrF_2$ | 41 | 50% |
| 4 | $BaF_2$ | 41 | 50% |
| 5 | $ZnF_2$ | 41 | 50% |
| 6 | $TiF_4$ | 41 | 50% |
| 7 | $ThF_4$ | 41 | 50% |
| 8 | $ZrF_4$ | 41 | 50% |
| 9 | $CaF_2$ | 4.1 | 5% |
| 10 | $CaF_2$ | 8.2 | 10% |
| 11 | $CaF_2$ | 12.3 | 15% |
| 12 | $CaF_2$ | 16.4 | 20% |

TABLE I-continued

| Example | Metal Fluoride | Parts | % Weight Metal Fluoride |
|---------|---------------|-------|------------------------|
| 13 | CaF$_2$ | 20.5 | 25% |

Examination of the catalysts so obtained by X-ray diffraction analysis confirmed that they consist of intimately mixed separate phases of γ-CrOOH gel catalyst and the metal fluoride.

In Examples 14–25, catalysts based on COT γ-CrOOH were prepared in a similar reaction vessel. In that vessel 134 parts of CrCl$_3$·6H$_2$O were dissolved in 5,000 parts water. To this was added 325 mesh metal fluoride with agitation, of the types and in the amounts indicated in Table II. The mixture was heated to 90° C. and then 188 parts concentrated aqueous ammonia (sp. gr. 0.90) were added dropwise while the heated solution was agitated. After one hour stirring, the precipitated solids were collected by filtration of the hot solution. The filter cake was washed twice with 200 parts cold deionized water, air dried and finally dried under vacuum at 100° C. The dry catalyst was then calcined at 250°–350° C.

TABLE II

| Example | Metal Fluoride | Parts | % by Weight Metal Fluoride |
|---------|---------------|-------|---------------------------|
| 14 | CaF$_2$ | 13 | 23.3 |
| 15 | MgF$_2$ | 13 | 23.3 |
| 16 | ThF$_4$ | 13 | 23.3 |
| 17 | TiF$_4$ | 13 | 23.3 |
| 18 | CdF$_2$ | 13 | 23.3 |
| 19 | AlF$_3$ | 42.7 | 50.0 |
| 20 | FeF$_3$ | 13 | 23.3 |
| 21 | CeF$_4$ | 13 | 23.3 |
| 22 | YF$_3$ | 13 | 23.3 |
| 23 | AlF$_3$ | 10.7 | 20.0 |
| 24 | BaF$_2$ | 42.7 | 50.0 |
| 25 | ZnF$_2$ | 42.7 | 50.0 |

The useful life of the catalysts was tested in an apparatus which consisted of a 1.905 cm. diameter by 30.48 cm. long Inconel tube vertically mounted in a constant temperature salt bath and having a thermocouple mounted in the center of the tube to measure catalyst bed temperatures. Refrigerant grade dichlorodifluoromethane from a commercial cylinder was fed via a standpipe through a cylinder containing liquid HF held in a constant temperature bath at 4° ± 0.2° C. This provides a constant mole ratio of HF to CF$_2$Cl$_2$ of 4/1. The CF$_2$Cl$_2$/HF mixture was fed to the bottom of the reactor. Products leaving the reactor were passed through 20% aqueous sodium hydroxide to remove acids, drying agents and then a wet test meter to measure volume of products as a function of time. Samples of the product stream after removal of acids were periodically taken for vapor phase chromatographic analysis.

In all tests, the following conditions prevailed:

| | |
|---|---|
| Catalyst weight: | 2g - 12/20 mesh |
| Flow rate CF$_2$Cl$_2$: | 10g/g catalyst/hr. |
| Reactant ratio HF/CF$_2$Cl$_2$: | 4/1 |
| Reactor temperature: | 400° C. |

To set a uniform, reproducible means for judging useful catalyst life, the criterion was selected that a useful catalyst would produce less and 1 volume percent unreacted CF$_2$Cl$_2$ in the product. When 1% was reached, the catalyst was considered no longer useful.

The test results for catalysts of this invention were compared with Control Examples A, B and C. Control Example A is a gel catalyst which was prepared in accordance with the procedure of Example 1A of Swamer et al., U.S. Pat. No. 3,258,500, except that the filter cake was dried at a temperature of about from 60° to 70° C. for a period of 24 hours and was not further activated. Control Example B was a COT catalyst prepared according to the procedure of Example 9 of Swamer et al., U.S. Pat. No. 3,258,500. Control Example C is a physical mixture of 50% preformed γ-CrOOH and calcium fluoride, each having a particle size of 12/20 mesh, which did not represent an intimate mixture of the present invention. The results of the testing are summarized in Table III.

TABLE III

CATALYST LIFE TESTS

| Example | Activity a (400° C.) | Life b Hours |
|---------|---------------------|--------------|
| Control A | 75–40 | 30 |
| Control B | 70–50 | 100 |
| Control C | 75–40 | 34 |
| 1 | 75–40 | 300–350 |
| 2 | 70–40 | 350 |
| 3 | c | — |
| 4 | c | — |
| 5 | c | — |
| 6 | 15–5 | 150 |
| 7 | 75–40 | 900 |
| 8 | Catalyst poisoned | — |
| 9 | — | 70 |
| 10 | — | 100 |
| 11 | — | 230 |
| 12 | — | 312 |
| 13 | — | 350 |
| 14 | 75–40 | 410 |
| 15 | 60–40 | 280 |
| 16A | 75–40 | 900+ |
| 16B | 70–40 | 3000 |
| 17 | 15–5 | ~150 |
| 18 | Catalyst poisoned | — |
| 19 | 85–40 | 950 |
| 20 | c | — |
| 21 | 60–40 | 900 |
| 22 | 60–40 | 900 |
| 23 | 85–40 | 1400 | a Volume percent CF$_4$ in product over test period, remainder CF$_3$Cl.
b Hours to appearance of 1% CF$_2$Cl$_2$ in product.
c Initial production approximately 50% CF$_3$Cl and less than 5% CF$_4$. Some quantities of CF$_2$Cl$_2$ were unconverted by each catalyst initially; negating the testing criteria used for catalyst life.

The catalysts of Examples 19, 20, 24 and 25 were tested in the same apparatus except that the feed streams of vinyl chloride and HF were maintained as separate streams until entering the reactor. HF was fed from the original container heated at 40° C. with flow measured by a "Hastings" flowmeter. Catalysts (12/20 mesh), reaction conditions and test results are shown in Table IV.

TABLE IV

| Examples | Temperature °C | HF/C₂H₃Cl Molar | Space Velocity, hr.⁻¹ | % Conversion C₂H₃Cl | % Yield CHF₂CH₃ | % Yield CH₂=CHF |
|---|---|---|---|---|---|---|
| 19A | 180 | 4.8 | 114 | 99 | 97.0 | 0.8 |
| 19B | 200 | 4.1 | 94 | 99 | 97.4 | 1.3 |
| 19C | 225 | 6.2 | 131 | 98 | 97.0 | 1.9 |
| 19D | 250 | 5.4 | 116 | 95 | 91.2 | 7.0 |
| 20A | 180 | 6.0 | 154 | 99 | 98.7 | 0.5 |
| 20B | 200 | 5.8 | 170 | 99 | 97.8 | 1.2 |
| 20C | 225 | 6.2 | 143 | 98 | 96.6 | 2.9 |
| 20D | 250 | 4.6 | 130 | 95 | 91.0 | 8.1 |
| 24A | 180 | 10.0 | 130 | 99 | 98.7 | 0.9 |
| 24B | 200 | 9.3 | 123 | 99 | 98.1 | 1.2 |
| 24C | 225 | 5.9 | 50 | 98 | 97.5 | 2.0 |
| 24D | 250 | 7.1 | 128 | 96 | 93.4 | 5.6 |
| 25A | 180 | 5.0 | 133 | 99 | 97.3 | 0.7 |
| 25B | 200 | 5.2 | 130 | 99 | 97.6 | 1.2 |
| 25C | 225 | 4.9 | 142 | 97 | 96.0 | 3.2 |
| 25D | 250 | 6.0 | 150 | 95 | 91.8 | 7.2 |

EXAMPLES 26 AND 27

Two catalysts were prepared substantially in accordance with the procedures of Examples 14–25. The catalysts of Examples 26 and 27 comprised γ-CrOOH COT catalyst with 50% and 20% AlF₃, respectively. These catalysts were compared to Control Examples D and E, which were substantially pure γ-CrOOH COT catalyst and AlF₃, respectively. The testing was conducted at different temperatures, and the results are reported in Table V. The catalyst containing 50% AlF₃ was found to be more active than γ-CrOOH catalyst while the catalyst containing 20% AlF₃ was less active. AlF₃ itself is substantially inactive for CF₄ production.

TABLE V

| Example | % CF₄ in Product | | | |
|---|---|---|---|---|
| | 300° C. | 350° C. | 400° C. | 450° C. |
| 26 | 9 | 20 | 80 | 70 |
| 27 | 1 | 10 | 35 | 50 |
| Control D | 2 | 15 | 70 | 70 |
| Control E | — | — | trace | — |

EXAMPLES 28 AND 29

Catalysts were prepared substantially in accordance with the procedures of Examples 20 and 19, respectively. These catalysts were used in the fluorination of chloroform in an apparatus which consisted of a 2.54 cm. diameter by 30.48 cm. nickel pipe vertically mounted in a constant temperature bath and having a thermocouple mounted in the center of the tube to measure catalyst bed temperature. The initial 1.27 cm. length at the inlet end of the pipe was used for gas mixing prior to entering the catalyst bed. Chloroform was fed into the mixing chamber with a syringe pump (100 ml. capacity). HF was fed from the original container heated at 40° C. with flow measured by a Hastings flowmeter. The reactor was maintained at 200° C. Product collection and analysis was as in Example 1. Catalyst (12/20 mesh) was activated in a stream of HF (650 ml./min. STP) at 200° C. for 5–10 hours before use. During tests, the chloroform feed rate was 55 g./hr. and the HF/CHCl₃ mole ratio was held at 4/1. The reactor held approximately 2 g. of catalyst. The catalysts were compared to Control Example F, a γ-CrOOH COT catalyst prepared substantially according to Swarner et al., U.S. Pat. No. 3,258,500, Example 9. The results are shown in Table IV.

TABLE IV

| | FLUORINATION OF CHLOROFORM | | |
|---|---|---|---|
| | Product, Volume % | | |
| Example | CHF₃ | CHClF₂ | CHCl₃ |
| Control F | 40 | 60 | 0 |
| 28 | 5 | 45 | 50 |
| 29 | ~100 | ~0 | ~0 |

I claim:

1. A catalyst comprising an intimate mixture of γ-CrOOH and about from 5% to 50% by weight of at least one non-alkaline metal fluoride selected from thorium tetrafluoride (ThF₄), aluminum trifluoride (AlF₃), calcium fluoride (CaF₂), magnesium fluoride (MgF₂), titanium tetrafluoride (TiF₄), cerium tetrafluoride (CeF₄), yttrium trifluoride (YF₃), strontium fluoride (SrF₂), barium fluoride (BaF₂), ferric fluoride (FeF₃) and zinc fluoride (ZnF₂).

2. A catalyst of claim 1 wherein the metal fluoride is selected from calcium fluoride, magnesium fluoride, thorium tetrafluoride, aluminum trifluoride, cerium tetrafluoride, and yttrium trifluoride.

3. A catalyst of claim 1 wherein the metal fluoride is selected from titanium tetrafluoride, strontium fluoride, barium fluoride, ferric fluoride and zinc fluoride.

4. A catalyst of claim 2 wherein the metal fluoride consists essentially of aluminum trifluoride.

5. A catalyst of claim 2 wherein the metal fluoride consists essentially of thorium tetrafluoride.

6. A catalyst of claim 1 wherein the γ-CrOOH has a particle size of less than about 5 microns and the metal fluoride has a particle size of less than about 44 microns.

7. A catalyst of claim 1 prepared by the precipitation of γ-CrOOH in the presence of metal fluoride particles.

8. A catalyst prepared by the precipitation of γ-CrOOH in the presence of particles of at least one non-alkaline metal fluoride selected from thorium tetrafluoride (ThF₄), aluminum trifluoride (AlF₃), calcium fluoride (CaF₂), magnesium fluoride (MgF₂), titanium tetrafluoride (TiF₄), cerium tetrafluoride (CeF₄), yttrium trifluoride (YF₃), strontium fluoride (SrF₂), barium fluoride (BaF₂), ferric fluoride (FeF₃) and zinc fluoride (ZnF₂), the particles comprising about from 5 to 50% by weight of the catalyst and exhibiting a particle size of less than about 44 microns.

* * * * *